United States Patent
Cheng et al.

(10) Patent No.: US 9,222,878 B2
(45) Date of Patent: Dec. 29, 2015

(54) METHOD AND DEVICE FOR OPTICAL IMAGING WITH A RESONANT AMPLIFIER ASSEMBLY

(71) Applicant: Purdue Research Foundation, West Lafayette, IN (US)

(72) Inventors: Ji-Xin Cheng, West Lafayette, IN (US); Mikhail N. Slipchenko, West Lafayette, IN (US); Robert A. Oglesbee, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 60 days.

(21) Appl. No.: 14/373,197

(22) PCT Filed: Jan. 20, 2013

(86) PCT No.: PCT/US2013/022348
§ 371 (c)(1),
(2) Date: Jul. 18, 2014

(87) PCT Pub. No.: WO2013/110023
PCT Pub. Date: Jul. 25, 2013

(65) Prior Publication Data
US 2014/0361150 A1   Dec. 11, 2014

Related U.S. Application Data

(60) Provisional application No. 61/589,079, filed on Jan. 20, 2012.

(51) Int. Cl.
*G01N 21/00* (2006.01)
*G01N 21/17* (2006.01)
(Continued)

(52) U.S. Cl.
CPC ............... *G01N 21/17* (2013.01); *G01B 9/04* (2013.01); *G01J 3/2803* (2013.01);
(Continued)

(58) Field of Classification Search
CPC ... G01N 21/17; G01N 21/65; G01N 2201/12; G01B 9/04; G01J 3/2803; G01J 3/44; G02B 21/16; G02B 21/002
See application file for complete search history.

(56) References Cited

FOREIGN PATENT DOCUMENTS

EP   1046900 A2   10/2000
EP   2253945 A1   11/2010
(Continued)

OTHER PUBLICATIONS

Slipchenko et al., 'High-Speed Vibrational Imaging and Spectral Analysis of Lipid Bodies by Compound Raman Microscopy', Journal of Phys. Chem. B, vol. 113, No. 21, pp. 7681-7686, 2009 (total 6 pgs.).

(Continued)

*Primary Examiner* — Tony Ko
(74) *Attorney, Agent, or Firm* — Lee & Hayes, PLLC; Christopher J. White

(57) ABSTRACT

An optical imaging apparatus includes an optical signal source, an optical signal detector apparatus, and a resonant amplifier assembly. The optical signal source is configured (i) to generate an optical signal including a carrier signal and an imaging signal, and (ii) to guide the optical signal to a sample. The optical signal detector apparatus is configured (i) to detect a modified optical signal from the sample, and (ii) to generate an electrical image signal based on the modified optical signal. The electrical image signal includes a background component and a modulated image signal corresponding to an image of the sample. The resonant amplifier assembly is electrically coupled to the optical signal detector apparatus and is configured (i) to isolate the modulated image signal from the background component, (ii) to amplify the modulated image signal, and (iii) to rectify the modulated image signal.

17 Claims, 14 Drawing Sheets

(51) Int. Cl.
  *G01N 21/65* (2006.01)
  *G02B 21/00* (2006.01)
  *G02B 21/16* (2006.01)
  *G01J 3/28* (2006.01)
  *G01J 3/44* (2006.01)
  *G01B 9/04* (2006.01)
  *G01J 1/46* (2006.01)

(52) U.S. Cl.
  CPC . *G01J 3/44* (2013.01); *G01N 21/65* (2013.01); *G02B 21/002* (2013.01); *G02B 21/16* (2013.01); *G01J 1/46* (2013.01); *G01N 2021/655* (2013.01); *G01N 2201/12* (2013.01)

(56) References Cited

FOREIGN PATENT DOCUMENTS

| WO | WO03029790 A1 | 4/2003 |
| WO | WO2011033285 A1 | 3/2011 |

OTHER PUBLICATIONS

Korean Intellectual Property Office (ISA/KR), International Search Report from PCT/US2013/022348 as completed May 7, 2013, (total 3 pgs.).

Korean Intellectual Property Office (ISA/KR), Written Opinion from PCT/US2013/022348 as completed May 7, 2013, (total 3 pgs.).

FIG. 13A
FIG. 13B
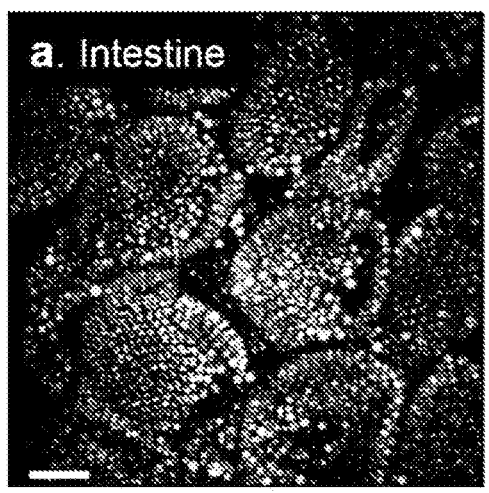
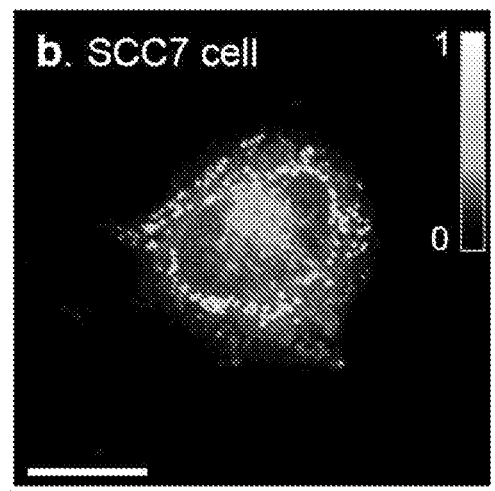
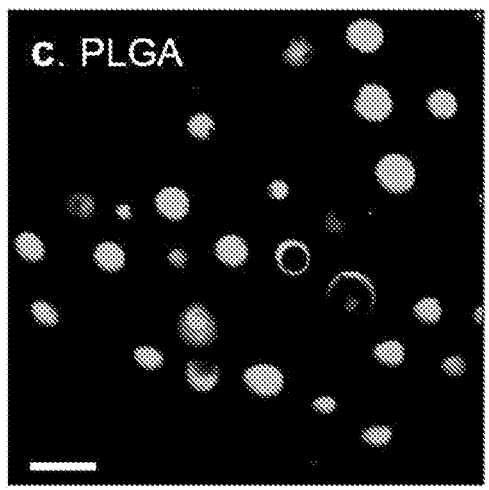
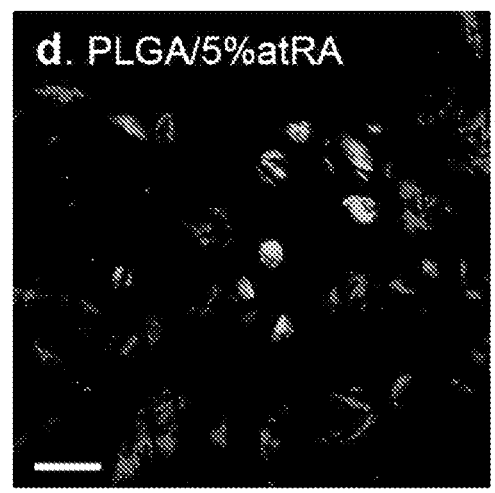
FIG. 13C
FIG. 13D

FIG. 15A     FIG. 15B     FIG. 15C
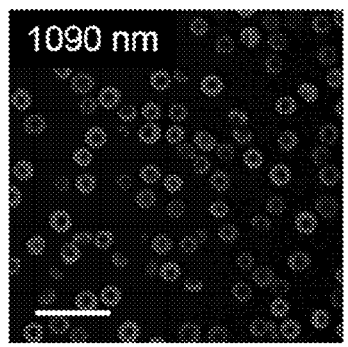 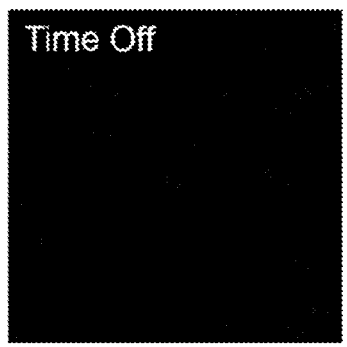 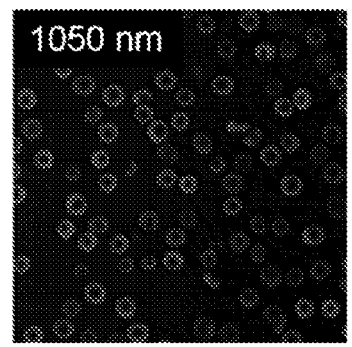
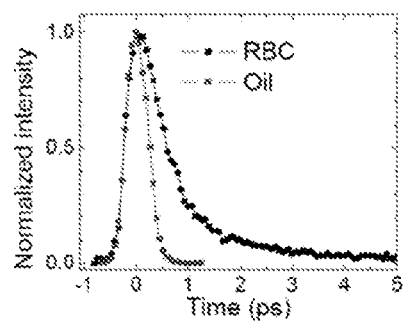 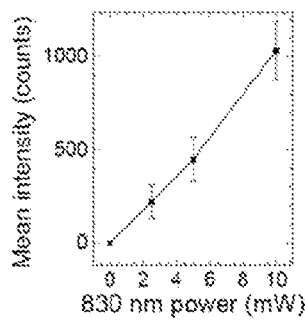 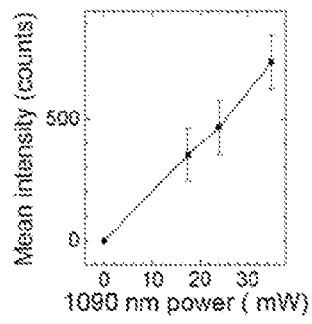
FIG. 15D     FIG. 15E     FIG. 15F

METHOD AND DEVICE FOR OPTICAL IMAGING WITH A RESONANT AMPLIFIER ASSEMBLY

This application claims the benefit of priority of U.S. provisional application Ser. No. 61/589,079, filed Jan. 20, 2012, the disclosure of which is incorporated by reference herein in its entirety.

FIELD

The present disclosure relates to microscopy apparatus and, in particular, to a signal processing device for an optical imaging apparatus that includes a resonant tank circuit.

BACKGROUND

One type of microscopy apparatus is an heterodyne detected optical imaging apparatus, which generates images of a sample based on the principle of vibrational or electronic spectroscopy without contacting or destroying the sample. These types of imaging apparatus are useful for imaging samples including biomass, pharmaceutical samples, lipid bodies, and nanomaterials, among other types of samples. Additionally, heterodyne detected optical imaging apparatus enable imaging of a sample without requiring labeling or staining of the sample.

In use, heterodyne detected optical imaging apparatus generate an electrical output signal that includes an amplitude modulated image data signal and a direct current signal from a local oscillator. Typically, the image data signal is extracted from the electrical output signal by a complex device referred to as a lock-in amplifier.

Lock-in amplifiers, also known as phase-sensitive detectors, have been in use since approximately 1961. Essentially, a lock-in amplifier is a phase-sensitive bandpass amplifier with a variable central frequency and bandwidth. Accordingly, the lock-in amplifier rejects the background signal (i.e. the direct current signal from the local oscillator), filters the image data signal from electrical noise, and then amplifies the image data signal to a desired amplitude for further signal processing. The image data signal is then processed by additional electrical components, such as an analog to digital converter.

While lock-in amplifiers are useful instruments for optical microscopy devices, such as the heterodyne detected optical image apparatus described above, this type of amplifier does exhibit some disadvantages. First, lock-in amplifiers exhibit a large thermal noise, which is detrimental to the signal to noise ratio ("SNR") of the electrical output signal. As an example, the SNR at low laser power (as is used with live cell imaging) is limited by the electrical noise produced by the Johnson-Nyquist noise of the input impedance of the lock-in amplifier's input preamplifier. Attempting to improve the SNR by increasing the input impedance only worsens the SNR for a MHz-modulated signal due to the input capacitance of the lock-in amplifier, among other factors. Second, lock-in amplifiers typically process the input signal more slowly than is desired by most users. For example, the widely used SR844 digital lock-in amplifier offered by Stanford Research Systems has a minimum time constant of approximately 20 µs. At such a time constant, it takes tens of seconds to obtain an image of 512×512 pixels. Third, lock-in amplifiers are complex and expensive devices, which set a bottleneck for the wide use of heterodyne detected nonlinear optical microscopy.

Accordingly, further developments based on one or more of the above-described limitations are desirable for heterodyne detected optical imaging apparatus.

SUMMARY

According to one embodiment of the disclosure, an optical imaging apparatus includes an optical signal source, an optical signal detector apparatus, and a resonant amplifier assembly. The optical signal source is configured (i) to generate an optical signal including a carrier signal and an imaging signal, and (ii) to guide the optical signal to a sample. The optical signal detector apparatus is configured (i) to detect a modified optical signal from the sample, and (ii) to generate an electrical image signal based on the modified optical signal. The electrical image signal includes a background component and a modulated image signal corresponding to an image of the sample. The resonant amplifier assembly is electrically coupled to the optical signal detector apparatus and is configured (i) to isolate the modulated image signal from the background component, (ii) to amplify the modulated image signal, and (iii) to rectify the modulated image signal.

According to another embodiment of the disclosure, a method of imaging a sample with an optical imaging apparatus includes generating an optical signal including a carrier signal and an imaging signal with an optical signal source, and guiding the optical signal to the sample with the optical signal source. The method further includes detecting a modified optical signal from the sample with an optical signal detector apparatus, and generating an electrical image signal based on the modified optical signal with the optical signal detector apparatus. The electrical image signal includes a background component and a modulated image signal corresponding to an image of the sample. The method still further includes isolating the modulated image signal from the background component with a resonant amplifier assembly, amplifying the modulated image signal with the resonant amplifier assembly, and rectifying the modulated image signal with the resonant amplifier assembly.

BRIEF DESCRIPTION OF THE DRAWINGS

FIG. 13A is an image of a portion of a mouse intestine as generated by the optical imaging apparatus of FIG. 1;

FIG. 13B is an image of an SCC7-cell with an intensive signal originating from small lipid droplets as generated by the optical imaging apparatus of FIG. 1;

FIG. 13C is an image of a PLGA microsphere without atRA as generated by the optical imaging apparatus of FIG. 1;

FIG. 13D is an image of a PLGA microsphere loaded with 5% atRA as generated by the optical imaging apparatus of FIG. 1;

FIG. 15A is a transient absorption image of red blood cells as generated by the optical imaging apparatus of FIG. 1;

FIG. 15B is a test image showing that the image of FIG. 15A was generated by transient absorption and not by photothermal processes;

FIG. 15C is an off-Raman resonance image of the red blood cells shown in FIG. 15A, showing that the image in FIG. 15A was generated by transient absorption and not by SRS;

FIG. 15D is a graph showing a normalized intensity versus time for both the red blood cells of FIG. 15A and a sample of olive oil;

FIG. 15E is a graph showing an intensity of a pump beam versus time corresponding the image of FIG. 15A; and FIG. 15F is a graph showing an intensity of a Stokes beam versus time corresponding to the image of FIG. 15A.

DETAILED DESCRIPTION

Figure 1:
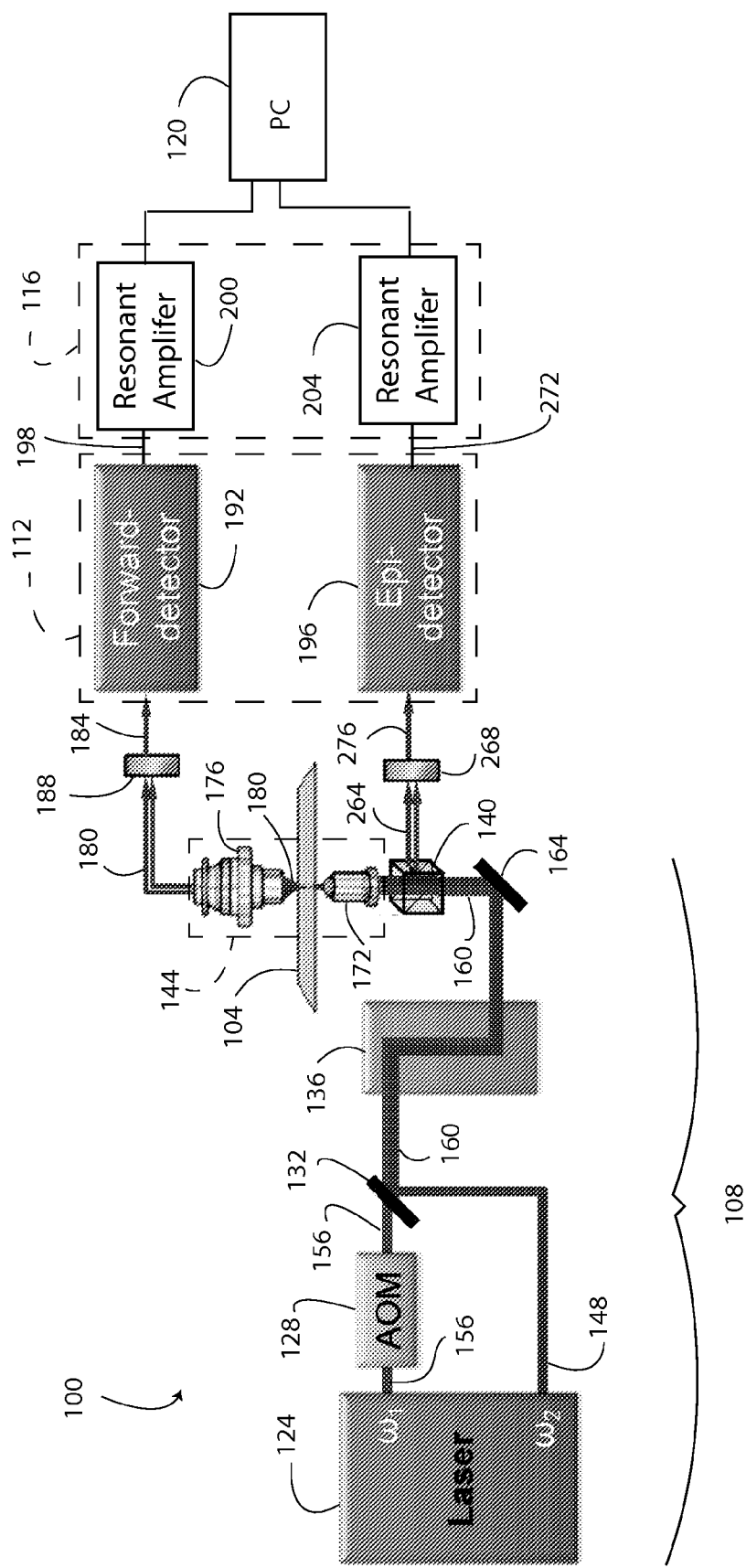
FIG. 1 is a block diagram view of an exemplary embodiment of an optical imaging apparatus connected to a personal computer.

As shown in FIG. 1, an optical imaging apparatus 100 is configured to generate a digital image of a sample 104. The optical imaging apparatus 100 is electrically connected to a personal computer 120. The optical imaging apparatus 100 includes an optical signal source 108, an optical signal detector apparatus 112, and a resonant amplifier assembly 116. As described herein, the optical imaging apparatus 100 includes the resonant amplifier apparatus 116, which reduces the cost and the complexity of the apparatus 100 compared to prior art imaging systems that rely on a lock-in amplifier alone. As will also be discussed below, the use of the resonant amplifier apparatus 116 further improves the signal to noise ratio ("SNR") of the resulting electrical signal produced by the apparatus 100.

The optical signal source 108, in this embodiment, includes a laser source 124, an acousto-optic modulator 128, an optical signal combiner 132, a laser scanning unit 136, a polarization beam splitter 140, and a lens assembly 144. The laser source 124 is configured to generate an optical signal that includes a carrier signal and an imaging signal. When the imaging apparatus 100 is configured, for example, for stimulated Raman scattering imaging ("SRS microscopy"), the carrier signal is referred to as a local oscillator signal or a pump beam 148, and the imaging signal is referred to a Stokes beam 152. The laser source 124 generates the pump beam 148 at a first angular frequency ($\omega_1$) and generates the Stokes beam 152 at a second angular frequency ($\omega_2$) that is different from the first angular frequency. In one embodiment, the pump beam 148 is generated at a wavelength tunable from 680 to 1080 nm (corresponding to the first angular frequency ($\omega_1$)) and the Stokes beam 152 is generated at a wavelength tunable from 1.0 to 1.6 μm (corresponding to the second angular frequency ($\omega_2$)).

The laser source 124 may suitably include at least one of a diode laser, an erbium doped fiber laser, a photonic crystal fiber, any other type of fiber laser, a fiber optical parametric oscillator, a Ti-sapphire oscillator, an optical parametric oscillator, soliton-based systems, or any other suitable device as desired by those of ordinary skill in the art. Furthermore, in another embodiment, the optical imaging apparatus 100 includes a laser source for generating the Stokes beam 152 and a separate laser source for generating the pump beam 148.

The acousto-optic modulator 128 is optically coupled to the laser source 124 and to the optical signal combiner 132. In particular, the acousto-optic modulator 128 is optically coupled to receive the Stokes beam 152 from the laser source 124. The acousto-optic modulator 128 is configured to control/modulate the intensity of the Stokes beam 152, by modulating the Stokes beam at a particular frequency, which is referred to herein as an optical modulation frequency ($\omega_o$). The Stokes beam 152 is referred to herein as a modulated Stokes beam 156 (or a modulated imaging signal) as it exits the acousto-optic modulator 128. Acousto-optic modulators, such as the acousto-optic modulator 128, are known to those of ordinary skill in the art.

With continued reference to FIG. 1, the optical signal combiner 132 is optically coupled to the acousto-optic modular 128, to the laser source 124, and to the laser scanning unit 136. More specifically, the optical signal combiner 132 is optically coupled to receive the pump beam 148 from the laser source 124 and to receive the modulated Stokes beam 156 from the acousto-optic modulator 128. The optical signal combiner 132 is configured to generate an optically combined optical signal 160 from the modulated Stokes beam 156 and the pump beam 148. To this end, the optical signal combiner 132 may suitably be a conventional device configured to collinearly overlap the modulated Stokes beam 156 and the pump beam 148.

The laser scanning unit 136 is optically coupled to the optical signal combiner 132 and to the polarization beam splitter 140. The laser scanning unit 136 is associated with reflectors 164, which are configured to move the combined optical signal 160 along a path of movement referred to herein as a scanning pattern. The movement of the combined optical signal 160 causes the combined optical signal 160 to strike an area of the sample 104 that is desired to be imaged.

The polarization beam splitter 140 is optically coupled to the laser scanning unit 136 and to the lens assembly 144. In particular, the polarization beam splitter 140 is optically coupled to receive the combined optical signal 160 from the laser scanning unit 136, and to provide a focused, combined optical signal onto a portion of the lens assembly 144.

Referring still to FIG. 1, the lens assembly 144 includes an objective lens 172 and a condenser 176. The objective lens 172 is positioned on one side of the sample 104 to receive the combined optical signal 160 from the polarization beam splitter 140. The objective lens 172 is conventionally configured to focus the combined optical signal 160 onto the sample 104. In one exemplary embodiment, the objective lens 172 is a 60× water-dipping objective lens. In another exemplary embodiment, the objective lens 172 is a 40× water-dipping objective lens.

The condenser 176 is positioned on an opposite side of the sample 104 from the objective lens 172. Accordingly, the condenser 176 is positioned to collect a modified optical signal 180 from the sample 104. The modified optical signal 180 is a forward-scattered signal, which includes a modified pump beam signal 184 and the modulated Stokes beam 156 (see FIG. 5, discussed further below). To this end, the objective lens 176 is configured to collect forward-scattered photons from the sample 104, which are used for forward-detection imaging. In one particular embodiment, in order to minimize the thermal lensing effect the condenser 176 is an oil-immersion condenser.

As shown in FIG. 1, the objective lens 176 is operably configured to provide the modified optical signal 180 to a filter device 188. The filter device 188 is an optical filter that is configured to pass light of only a particular range of frequencies. Specifically, the filter device 188 passes light corresponding to the frequency ($\omega_2$) of the modified pump beam 184 and blocks or rejects light corresponding to the frequency ($\omega_1$) of the Stokes beam 152.

The optical signal detector apparatus 112 includes a forward detector unit 192 and an epi-detector unit 196, which are both heterodyne detectors, in this embodiment. The forward detector unit 192 is positioned to receive the modified optical signal 180 (i.e. the forward-scattered component of the signal) from the sample 104. In particular, the forward detector unit 192 is operably configured to detect the modified pump beam signal 184 from the filter device 188. The forward detector unit 192 includes a photodiode 232 (see FIG. 3) that generates an electrical current in response to being illuminated. The photodiode 232 exhibits a nonlinear response to the modified pump beam signal 184. The forward detector unit 192 and the epi-detector unit 196 are located in the same housing; alternatively, the units 192, 196 are located in separate housings. The forward detector unit 192 is configured to generate an electrical image signal 198 that is based on the modified pump beam signal 184. The electrical image signal 184 includes a background component and a modulated image signal. The background component includes a direct current signal from the pump beam 148 and also typically includes electrical noise. The modulated image signal is an electronic signal that corresponds to an image of the sample.

Figure 2:
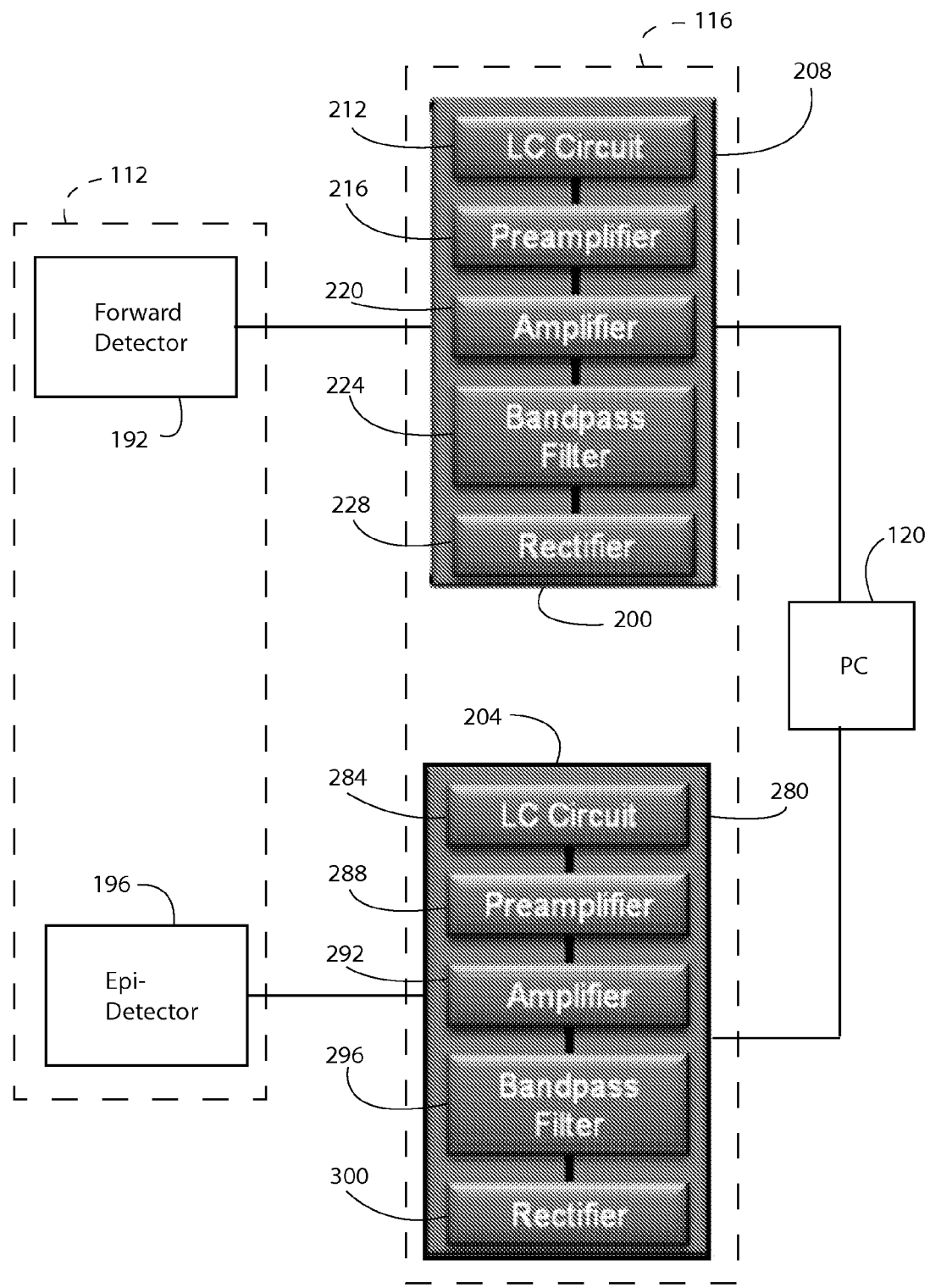
FIG. 2 is a block diagram view of an optical signal detector apparatus and a resonant amplifier assembly of the optical imaging apparatus of FIG. 1.

The resonant amplifier assembly 116 includes a forward resonant amplifier unit 200 and an epi-resonant amplifier unit 204. FIG. 2 provides additional detail regarding the forward resonant amplifier unit 200 and the epi-resonant amplifier unit 204. Referring now to FIG. 2, the forward resonant amplifier unit 200 is positioned in a housing 208, is electrically coupled to the forward detector unit 192, and is configured to receive the electrical image signal 198. The housing 208, in one embodiment, is approximately 4×2×1.5 inches in size, making it much smaller than the housing of the typical lock-in amplifier.

Figure 3:
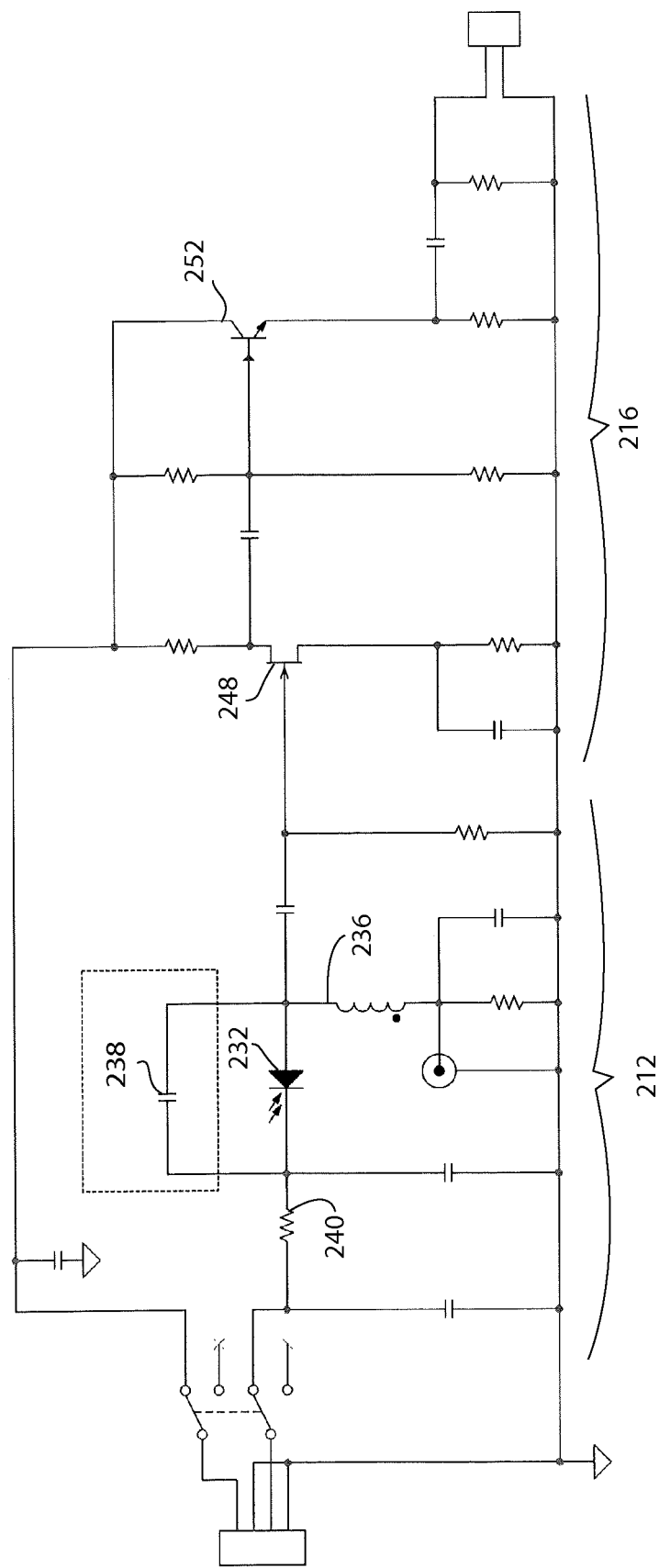
FIG. 3 is a schematic view of a portion of the resonant amplifier assembly of FIG. 2.

As shown in FIG. 2, the forward resonant amplifier unit 200 includes a resonant tank circuit 212 (series LC circuit, parallel LC circuit, series RLC circuit, or parallel RLC circuit), a preamplifier 216, a main amplifier 220, a bandpass filter 224, and a rectifier assembly 228, each of which is positioned in the housing 208. FIG. 3 shows in further detail the resonant tank circuit 212 and the preamplifier 216 of the forward resonant amplifier unit 200, as well as relevant portions of the forward detector unit 192.

Referring to FIG. 3, the resonant tank circuit 212 is electrically coupled to the photodiode 232 of the forward detector unit 192. The resonant tank circuit 212, in this embodiment, is a series resonant circuit, which includes an inductor 236 (or inductors) having an inductance L, a capacitor 238 (or capacitors) having a capacitance C, and a resistor 240 (or resistors) having a resistance R. In at least one embodiment, the capacitor 238 represents the parasitic capacitance of the photodiode 232. Accordingly, in such an embodiment, the magnitude of the capacitance C of the resonant tank circuit 212 is based on the physical structure of the photodiode 232, among other factors. In another embodiment, the capacitor 238 of the resonant tank circuit 212 includes additional capacitors (not shown) connected serially or in parallel with the photodiode 232, such that the magnitude of the capacitance C of the resonant tank circuit is a combined capacitance of the parasitic capacitance of the photodiode and at least one other discrete capacitor component connected thereto.

The resonant tank circuit 212 is tuned to the optical modulation frequency ($\omega_o$). In particular, the value of the inductor 236 (or the total inductance) is selected such that $\omega_o = 1/\sqrt{LC}$. The resonant tank circuit 212 is typically tuned by selecting the value of the inductor 236 since, as described above, the parasitic capacitance of the photodiode 232 is typically a fixed value for a given range of input signals to the photodiode. The resonant tank circuit 212 exhibits a quality factor (Q) and a bandwidth ($\Delta\omega$), as given by the following equations, $Q = (1/R)\sqrt{L/C}$, and $\Delta\omega = \omega_o/Q$. Accordingly, for high-speed imaging applications the value of the resistor 240 (or the total resistance) is in the tens of kOhms, as compared to the typical 50 Ohm input resistance of a lock-in amplifier.

The preamplifier 216 is electrically coupled to the resonant tank circuit 212 and to the main amplifier 220. The preamplifier 216 includes a junction gate field-effect transistor ("JFET") 248 and a bipolar junction transistor ("BJT") 252, among other components. In one embodiment, the resonant tank circuit 212 and the preamplifier 216 provide a gain to the electrical imaging signal 198 of about 22 dB.

Referring again to FIG. 2, the main amplifier 220 is electrically coupled to the preamplifier 216 to receive the amplified signal therefrom. In one embodiment, the main amplifier 220 is a selectable gain amplifier, which is configured to amplify the electrical signal output from the preamplifier 216. The gain of the main amplifier 220 is selected so as to amplify the electrical image signal 198 without saturating the main amplifier 220. The main amplifier 220 is provided as any selectable gain amplifier, as desired by those of ordinary skill in the art. In one particular embodiment, the main amplifier 220 has at least four gain settings from 19 dB to 58 dB and includes two operational amplifiers with a buffer stage on the output.

The bandpass filter 224 is electrically coupled to the main amplifier 220 to receive the amplified signal therefrom. The bandpass filter 224 has a center frequency that is approximately equal to the optical modulation frequency ($\omega_o$) of the Stokes beam 152. In one embodiment (not shown), to minimize amplifying the contribution from low and high frequency parasitic signals and noise, the bandpass filter 224 is a $3^{rd}$ order Butterworth bandpass filter with 2 MHz bandwidth at half-power points (−3 dB gain). Also, in another embodiment (not shown), the bandpass filter 224 is positioned between the preamplifier 216 and the main amplifier 220 in order to filter the signal from the preamplifier before the signal is amplified by the amplifier. Without the bandpass filter 224, the transmission type background would appear in the images generated by the imaging apparatus 100 due to the low frequency intensity modulation of the pump beam 148 by sample morphology.

The rectifier assembly 228 is electrically coupled to the bandpass filter 224. The rectifier assembly 228 is a full wave precision rectifier having a dynamic range of approximately 40 dB.

The electrical output signal of the forward resonant amplifier unit 200 is electrically coupled to the personal computer 120. The personal computer 120 includes an analog to digital converter (not shown) for converting the electrical output signal of the forward resonant amplifier unit 200 from an analog signal into a digital signal. Additionally, the personal computer 120 includes software that converts the digital signal into an image (typically magnified) of the sample. In another embodiment, the analog to digital converter is separate from and electrically coupled to the personal computer 120. To this end, the personal computer 120 includes a processing circuit, not shown, but which is conventional in general purpose computers, and memory for storing program instructions that make up the software.

With reference again to FIG. 1, in addition to collecting the forward-scattered photons from the sample 104, the optical imaging apparatus 100 includes components to collect the back-scattered photons through an epi-detection imaging process. In particular, the objective lens 172 is configured to receive back-scattered photons from the sample in response to illuminating the sample 104 with the combined optical signal 160. The objective lens 172 is operably configured to focus the back-scattered photons onto the polarization beam splitter 140.

The polarization beam splitter 140 is further configured to collect the back-scattered photons and split a back-scattered optical signal 264 (including the back-scattered photons, and referred to herein as a back-scattered component) away from the combined optical signal 160. The beam splitter 140 is configured to split the back-scattered optical signal 264 from the combined optical signal 160, based on the principle that the back-scattered optical signal 264 has a scrambled polarization unlike the combined optical signal 160.

After being spilt by the polarization beam splitter 140, the back-scattered optical signal 264 passes through a filter device 268. The filter device 268 is an optical filter that is configured to pass light of only a particular range of frequencies. Specifically, the filter device 268 passes light corresponding to the frequency of the modified pump beam 184 and blocks or rejects light corresponding to the frequency of the Stokes beam 152. The optical signal passed by the filter device 268 is referred to as a back-scattered modified pump beam signal 276.

The epi-detector unit 196 is positioned to receive the back-scattered modified pump beam signal 276 from the filter 268. The epi-detector unit 196 is substantially identical to the forward detector unit 192 and is configured to generate an electrical current in response to being illuminated in the same way that the forward detector unit generates an electrical current. Specifically, the epi-detector unit 196 generates an electrical image signal 272 that is based on the back-scattered modified pump beam signal 276.

The epi-detector unit 196 provides the electric image signal 272 to the epi-resonant amplifier unit 204. In particular, referring again to FIG. 2, the epi-resonant amplifier unit 204 is positioned in a housing 280, is electrically coupled to the epi-detector unit 196, and is configured to receive the electrical image signal 272. The housing 280, in one embodiment, is approximately 4×2×1.5 inches in size, making it much smaller than the typical the lock-in amplifier.

The epi-resonant amplifier unit 204 includes a resonant tank circuit 284, a preamplifier 288, an amplifier 292, a bandpass filter 296, and a rectifier assembly 300, each of which is positioned in the housing 280. The components of the epi-resonant amplifier unit 204 are substantially identically to, and function substantially the same as, the components of the forward resonant amplifier unit 200. The frequency to which the resonant tank circuit 284 is tuned is, in some embodiments, different from the frequency to which the resonant tank circuit 212 is tuned. The epi-resonant amplifier unit 204 is configured to amplifier a smaller magnitude of current as is typically associated with the signal from the epi-detector unit 196. The output signal of the epi-resonant amplifier unit 204 is electrically coupled to the personal computer 120 and is used to form the image of the sample 104.

Figure 4:
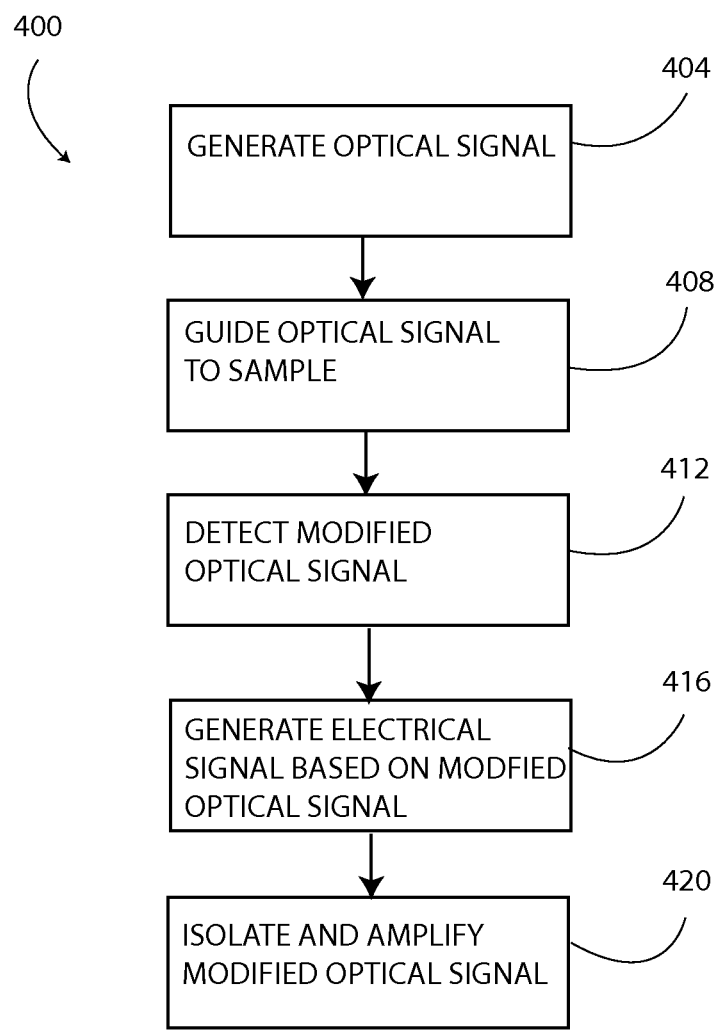
FIG. 4 is a flowchart depicting an exemplary method of operating the optical imaging apparatus of FIG. 1.

In operation, the optical imaging apparatus 100 is used to generate a digital image corresponding to a magnified view of the sample 104 according to the method 400 shown in the flowchart of FIG. 4. In block 404, the optical imaging apparatus 100 generates an optical signal (i.e. the pump beam 148 and the Stokes beam 152) with the laser source 124.

Figure 5:
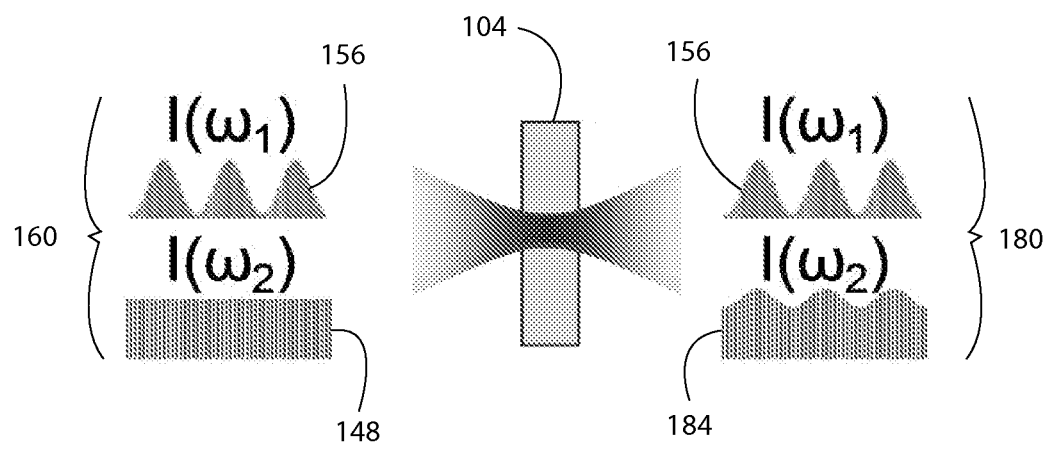
FIG. 5 is a diagram showing a combined optical signal and a modified optical signal formed from a sample being imaged with the optical imaging apparatus of FIG. 1.

Next, the acousto-optic modulator 128 modulates the Stokes beam 152. In the exemplary embodiment described herein, the Stokes beam 152 is modulated with 70% modulation depth at a 6 MHz frequency. In other embodiments, the modulation depth and frequency are different. In FIG. 5, the amplitude of the modulated Stokes beam 156 and the pump beam 148 are plotted as a function of time.

After modulation, the optical signal combiner 132 receives the modulated Stokes beam 156 and the pump beam 148 and combines the modulated Stokes beam and the pump beam into the combined optical signal 160. Next, the laser scanning unit 136 receives the combined optical signal 160 and moves the signal 160 in the scanning pattern over an area that includes the desired imaging area of the sample. Thereafter, the polarization beam splitter 140 receives the combined optical signal 160. The polarization beam splitter 140 guides the signal 160 to the objective lens 172 of the lens assembly 144.

As shown in block 408, the objective lens 172 of the lens assembly 144 guides and focuses the combined optical signal 160 on the sample 104 as it is moved in the scanning pattern by the laser scanning unit 136. When the photons of the combined optical signal 160 are beamed at the sample 104, molecular vibrations of the sample cause some of the photons to "back scatter," and the molecular vibrations cause other photons of the signal 160 to "forward scatter."

The scattered photons of the combined optical signal 160 carry information that corresponds to an image of the sample 104. For this reason, the forward-scattered photons are collected by the condenser 176 as the signal referred to herein as the modified optical signal 180. In FIG. 5, the amplitude of the modified optical signal 180 (including the modulated Stokes beam 156 and the modified pump beam signal 184) is plotted as a function of time. As described below, the back-scattered photons are also collected for imaging purposes as the signal referred to herein as the back-scattered optical signal 264.

After being collected by the condenser 176, the modified optical signal 180 is filtered by the filter device 188. The filter device 188 filters the modulated Stokes beam 156 from the modified optical signal 180, leaving only the modified pump beam signal 184 to pass through.

Next, as shown in block 412, the modified pump beam signal 184 is detected by the forward detector unit 192 and is converted into an electrical signal. In block 416, when the modified pump beam signal 184 illuminates the photodiode 232 of the forward detector unit 192, the forward detector unit generates the electrical image signal 198, which is an oscillating electrical signal that is based on the intensity and the phase of the signal 184. Therefore, the electrical signal 198, like the modified optical signal 180 and the modified pump beam signal 184, corresponds to an image of the sample 104.

In block 420, the forward resonant amplifier unit 200 processes the electrical image signal 198. The electrical signal 198, as described above, includes the background component and the modulated image signal. The resonant amplifier unit 200 isolates the modulated image signal from the background component, amplifies the modulated image signal, and then rectifies the modulated image signal.

First, the resonant tank circuit 212 isolates and/or "extracts" a small modulation of the local oscillator (i.e. the modulated image signal) riding on the top of a strong DC component (i.e. the background component). The change in current of the extracted modulation ("$\Delta I$") over the current of the DC component ("I") is less than or equal to $10^{-4}$ ($\Delta I/I \leq 10^{-4}$). Second, the modulated image signal as isolated by the resonant tank circuit 212 is amplified by the preamplifier 216 and the main amplifier 220. Third, the modulated image signal is filtered by the bandpass filter 224, in order to eliminate low and high frequency noise leaking through the resonant tank circuit 212, and then the modulated image signal is rectified by the rectifier assembly 228.

Figure 6:
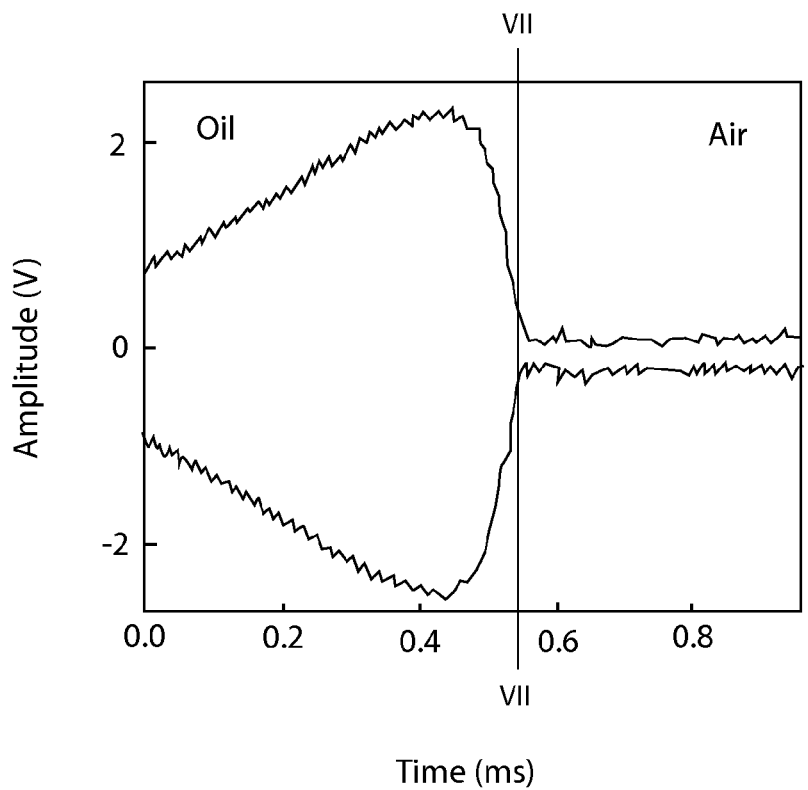
FIG. 6 is a graph showing a line scan across an oil/air interface of an electrical image signal as amplified by the resonant amplifier assembly of the optical imaging apparatus of FIG. 1.
Figure 7:
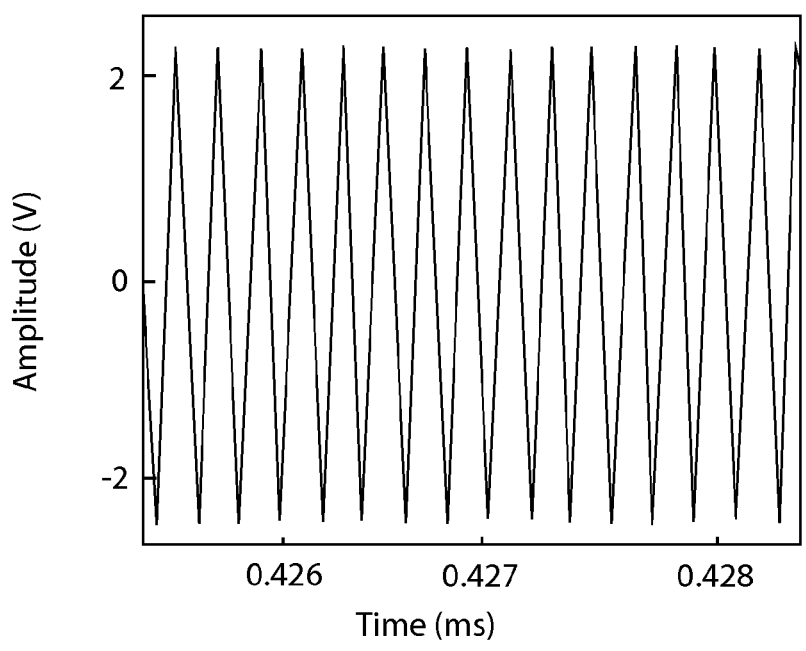
FIG. 7 is a graph showing a zoomed-in view of the line scan centered about line VII-VII of FIG. 6.
Figure 8:
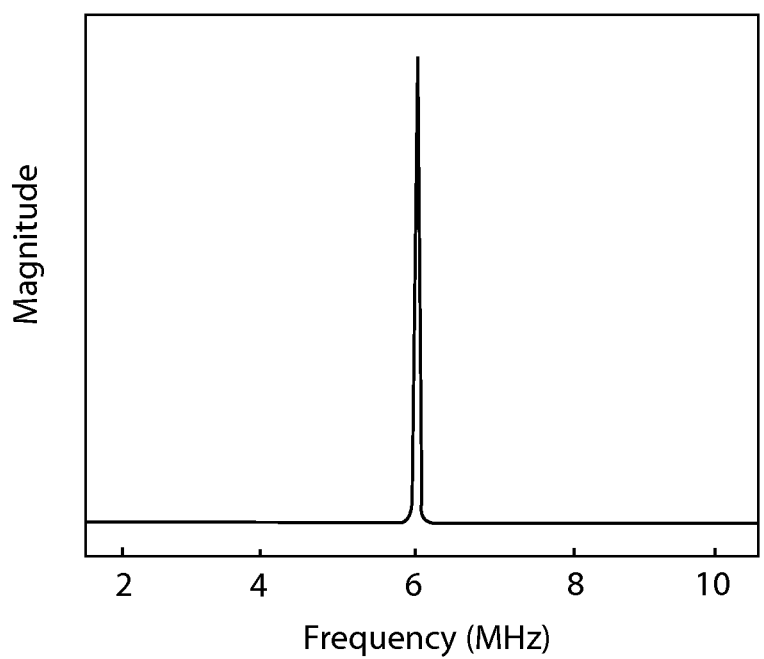
FIG. 8 is a graph showing the frequency response of the line scan of FIG. 7 centered about an optical modulation frequency of 6 MHz.

As shown in FIGS. 6-8, the output of the resonant amplifier unit 200 is an isolated, amplified, filtered, and rectified version of the modulated image signal, which is centered about the optical modulation frequency ($\omega_o$). To illustrate, in FIG. 6, a line scan across an oil/air interface is shown, as recorded by a fast oscilloscope (not shown) before the signal has reached the rectifier assembly 228. The oscilloscope trace shows a large amplitude corresponding to a signal from the oil and a small amplitude corresponding to a signal from the air. As shown in FIG. 7, zooming in on the trace of FIG. 6 at the line VII-VII shows the periodic oscillations of the modulated signal. With reference to FIG. 8, the periodic oscillations are confirmed to be at the optical modulation frequency by taking a fast Fourier transform of the signal, which is centered about the 6 MHz mark.

The rectified signal from the resonant amplifier unit 200 is received by the personal computer 120, which digitizes the analog signal into a digital electrical signal. The digital electrical signal is further processed by the execution of imaging software stored in memory, not shown, in the personal computer 120. The processing circuit of the personal computer 120, executing the imaging software, generates an image of the sample 104. The image(s) is displayable on a display module (not shown), such as a computer monitor or a television screen or is savable to the computer memory.

In a substantially identical manner, the epi-detector unit 196 and the epi-resonant amplifier unit 204 convert the back-scattered modified pump beam signal 276 into an image of the sample 104 suitable for display on the personal computer 120 or storage on a computer memory. One difference between the processing of the forward-scattered modified optical signal 180 and the back-scattered optical signal 264, is that the preamplifier 288 and amplifier 292 have more gain than the preamplifier 216 and the main amplifier 220 due to the modulated image signal portion of the electrical image signal 272 typically having a lower magnitude of current than the electrical image signal 198.

Figure 9:
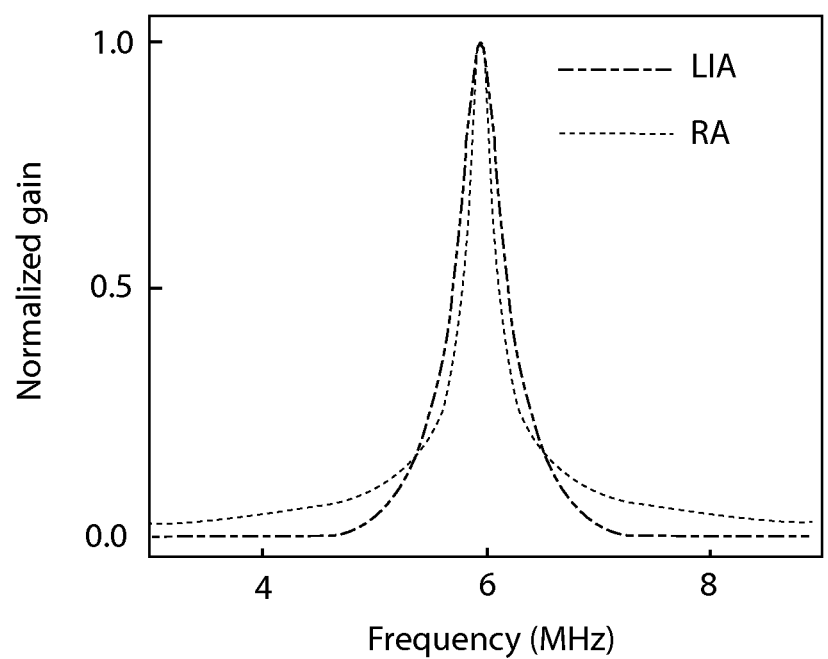
FIG. 9 is a graph showing the bandwidth of a resonant amplifier unit of the resonant amplifier assembly of FIG. 2 and the bandwidth of a typical lock-in amplifier.

The optical imaging apparatus 100 having a resonant amplifier assembly 116 offers advantages over other imaging apparatus that include a lock-in amplifier. As shown in FIG. 9, the bandwidth of the resonant amplifier unit 200, 204 is plotted against the bandwidth of a typical lock-in amplifier, specifically a Zurich Instruments model HF2LI lock-in amplifier (not shown, abbreviated as "LIA" in some of the figures). The resonant tank circuit 212 is tuned to have a resonant frequency of 6 MHz, and the measured bandwidth (full width at 0.707 maximum) of the circuit 212 is approximately 250 kHz. The lock-in amplifier, which is configured with a 1 µs time constant, exhibits a bandwidth of approximately 360 kHz at a frequency of 6 MHz.

Figure 10:
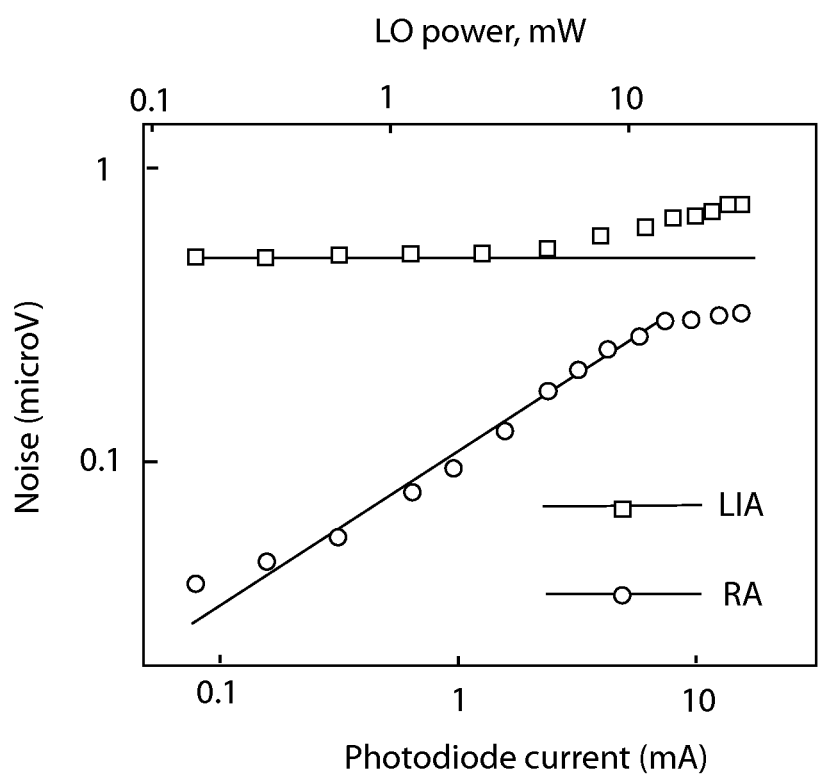
FIG. 10 is a graph showing a voltage level of an electrical noise signal verses a photodiode current and local oscillator power for both the optical imaging apparatus of FIG. 1 and the typical lock-in amplifier.

As shown in FIG. 10, the noise generated by the resonant amplifier unit 200, 204 and the noise generated by the lock-in amplifier is plotted versus photodiode current. The plot of the noise generated by the lock-in amplifier remains constant (i.e. "plateaus") from 0 mA to 2 mA of photodiode current and then slowly increases with photodiode current. The plateau is a result of the dominant electric noise at low current levels. The plot of the noise generated by the resonant amplifier unit 200, 204 shows a square root dependence (slope=0.5, in log scale) on the photodiode current from 0.1 mA to 0.7 mA, which indicates true laser shot noise limited detection. The plot confirms that compared to the lock-in amplifier, the resonant amplifier unit 200, 204 generates much less noise for a given photodiode current for currents ranging from 0.1 mA to 10 mA. Accordingly, the resonant amplifier unit 200, 204 is able to perform SRS imaging with lower power sources such as Er fiber lasers, photonic crystal fiber, fiber optical parametric oscillators, and the like.

Figure 11:
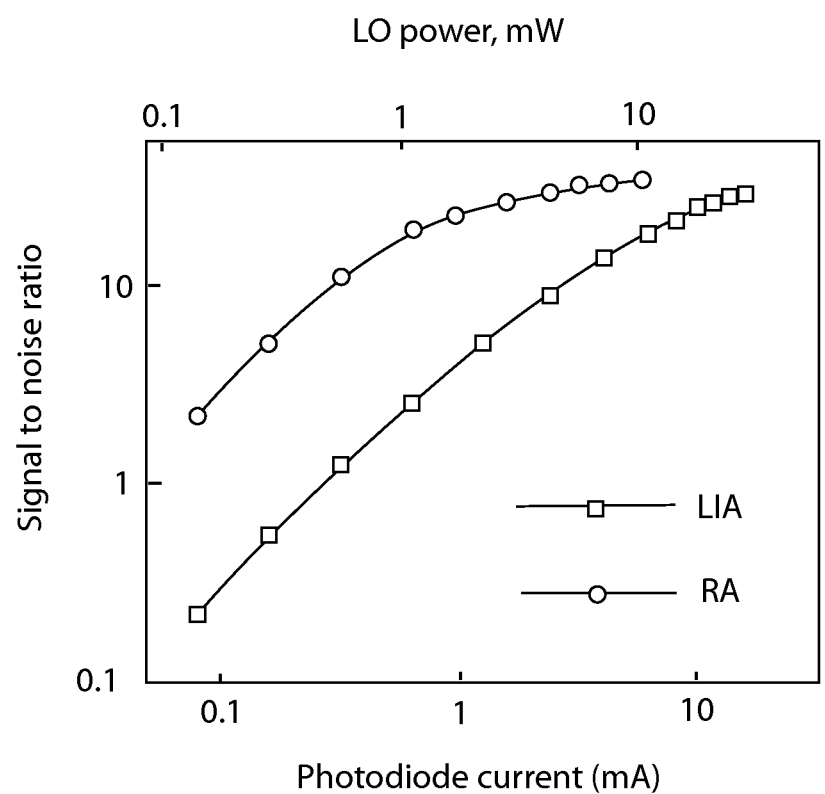
FIG. 11 is a graph showing signal to noise ratio verses photodiode current for both the optical imaging apparatus of FIG. 1 and the typical lock-in amplifier.

With reference to FIG. 11, the signal to noise ratio ("SNR") of the electrical signal generated by the resonant amplifier unit 200, 204 and the lock-in amplifier is plotted versus photodiode current. For a given photodiode current, the signal generated by the resonant amplifier unit 200, 204 has a SNR that is an order of magnitude lower than the SNR of the signal generated by the lock-in amplifier for photodiode currents from 0.1 mA to 1 mA. For photodiodes currents above 1 mA, the SNR of the resonant amplifier unit 200, 204 is still significantly lower than the lock-in amplifier. The increased SNR of the signal generated by the resonant amplifier unit 200, 204 is at least partially based on the increased input resistance of the resonant amplifier unit, as compared to the lock-in amplifier.

Figure 12:
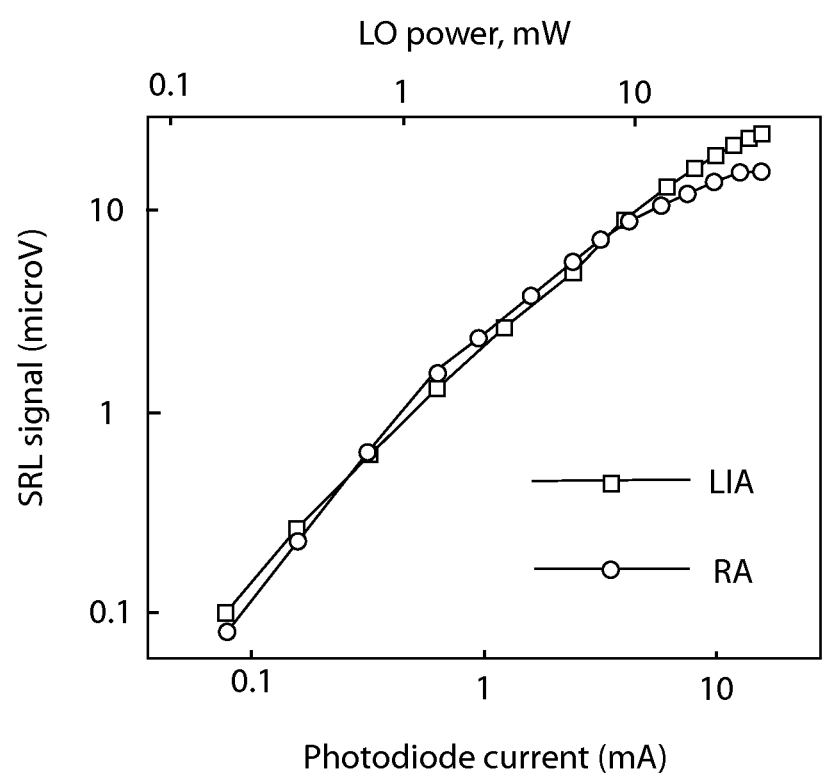
FIG. 12 is a graph showing a voltage level of an electrical signal versus a photodiode current and local oscillator power for both the optical imaging apparatus of FIG. 1 and the typical lock-in amplifier.

As shown in FIG. 12, the electrical output signal from the resonant amplifier unit 200, 204 is plotted against the electrical output signal from the lock-in amplifier. As shown, both devices exhibit a similar linearity in response to current from the detector 192, 196 (i.e. current from the photodiode 232). In particular, the resonant amplifier unit 200, 204 exhibits a dynamic range for linear response from 0.1 mA to 7.0 mA, which corresponds to 0.2 mW to 14 mW of local oscillator (i.e. the pump beam 148) power at the detector unit 192, 196. In principle, the linear response is extendable for higher power signals of the local oscillator by reducing the value of a current limiting resistor in the preamplifier. The linear response is extendable for lower power signals of the local oscillator by increasing the gain of the amplifier 292.

The above comparisons demonstrate that the resonant amplifier unit 200, 204 generates an electrical output signal that is superior to the lock-in amplifier. Significantly, the resonant amplifier unit 200, 204 is much less expensive, is much smaller in size, and is much less complex than the lock-in amplifier, thereby making the resonant amplifier unit 200, 204 a desirable and cost-effective amplifier unit for microscopy applications.

FIGS. 13A-13D show four exemplary images generated by the optical imaging apparatus 100. FIG. 13A shows a femtosecond SRL (Stimulated Raman Loss) image of triacylglycerol pools stored in the enterocytes of a portion of the small intestine of a mouse. The image is based on the signal from C—H stretch vibration. FIG. 13B shows another image produced by the optical imaging apparatus 100, which is an SRL image of SCC7-cell with an intensive signal originating from small lipid droplets. Without damage to the cells, trafficking of small LDs in live cells was monitored in real time.

The capability of the optical imaging apparatus 100 to perform fingerprint SRL imaging was tested by using drug distribution in poly(lactic-co-glycolic acid) ("PLGA") microspheres. As a biodegradable and biocompatible polymer, PLGA has been frequently used in microencapsulation of bioactive molecules such as all-trans retinoic acid ("atRA"). Based on their distinctive Raman bands, PLGA and atRA in the microspheres were mapped by SRL, generated by a five picosecond laser source.

FIGS. 13C and 13D show the SRL image of PLGA microspheres without atRA and loaded with 5% at RA, respectively, obtained at the speed of 2 μs/pixel. In the absence of atRA, the PLGA exhibited a spherical shape. At 5% atRA loading, the drug molecules did not blend with PLGA and were found mostly on the surface of irregular micro-particles. These data show the potential for the optical imaging apparatus 100 for pharmaceutical applications, such as the above, as well as, transient absorption imaging of heme proteins in red blood cells (RBCS) (See description of FIGS. 15A-15E).

Figure 14A:
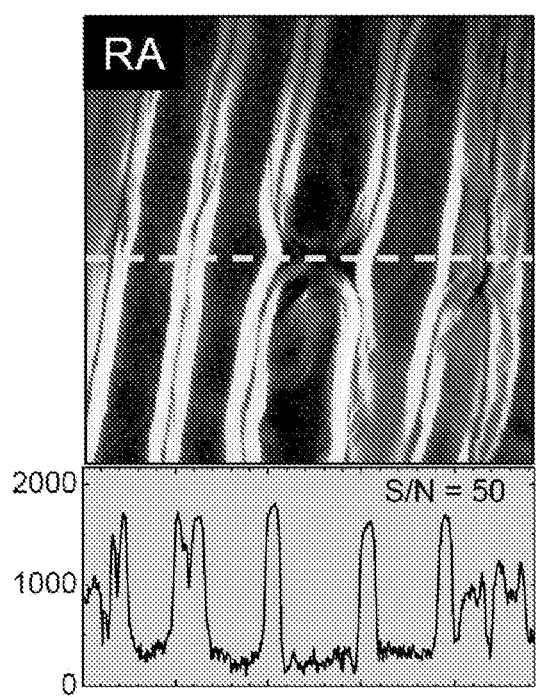
FIG. 14A is a graph and a corresponding image of axonal myelin as generated by the optical imaging apparatus of FIG. 1.
Figure 14B:
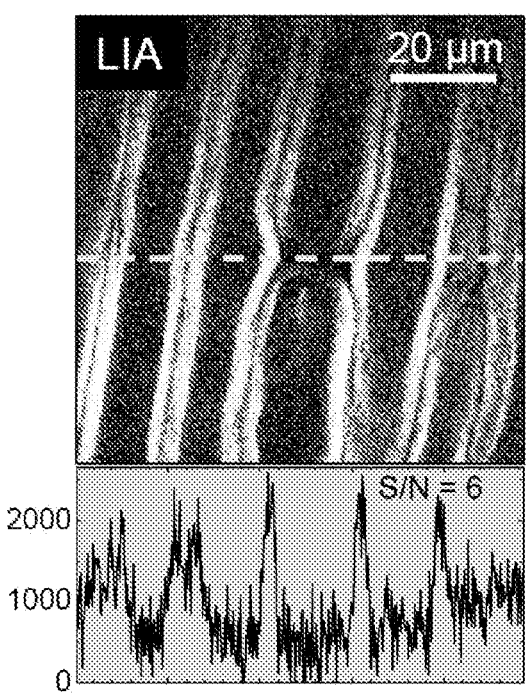
FIG. 14B is a graph and a corresponding image of axonal myelin as generated by the typical lock-in amplifier.

With reference to FIGS. 14A and 14B, the capability of the optical imaging apparatus to perform epi (backwards) detection is important for, among other reasons, in vivo imaging applications. In epi-detection the current generated by the photodiode of the epi-detector unit 196 is much smaller than in forward detection. As shown in FIG. 14A, based on the intensity profiles along the dashed lines, the epi-detected femtosecond SRL signal of axonal myelin obtained with the optical imaging apparatus resulted in an SNR of 50 (S/N=50). In comparison, imaging the same sample with the lock-in amplifier shows a much lower SNR of 6 (S/N=6) due to the electronic noise contribution. Accordingly, the optical imaging apparatus 100 improved the SNR by 8.3 times and enabled ex vivo 3D mapping of axonal myelin with high quality.

With reference to FIGS. 15A-15D, the optical imaging apparatus 100 was used to generate resonant amplifier based transient absorption images of red blood cells. Specifically, FIG. 15A shows an image of red blood cells formed by two synchronized femtosecond (fs) laser beams. To confirm that the image of FIG. 15A originated from transient absorption, and not from a photothermal effect, the probe beam was delayed by 10 picoseconds (ps) and, as shown in FIG. 15B, the signal nearly disappeared.

To determine if the signal of FIG. 15A includes a stimulated Raman scattering (SRS) contribution, the image formed on resonance with C—H vibration (i.e. FIG. 15A) was compared to an off-resonance image (i.e. FIG. 15C). In the comparison, the same level of intensity was observed, which confirms that the SRS contribution is negligible. To further confirm the two-photon two-color absorption mechanism, the signal intensity as a function of pump beam and probe beam powers was measured and was found to have a linear dependence, as shown in FIGS. 15E and 15F. Furthermore, as additional evidence of the transient absorption origin of the image of FIG. 15A, a scan of probe delay of the red blood cells was performed and was compared to a scan of probe delay of olive oil, for which a strong SRS signal is typically expected. As shown in FIG. 15D, a slow decay on the order of one picosecond for the signal from red blood cells was observed in contrast to a substantially instantaneous response for the SRL signal from the olive oil. Taken together, the above examples and results demonstrate that the optical imaging apparatus 100 is applicable to pump probe imaging as well as time-resolved spectroscopy studies. In the above examples, the pump wavelength was fixed at 830 nm, and the Stokes wavelength was tuned to 1090 nm for C—H resonance and 1050 nm for off C—H resonance. Also, an imaging speed of 8 μs/pixel was used. The Stokes and pump beam powers at the sample were 24 mW and 6 mW, respectively.

In another embodiment of the optical imaging apparatus 100, the optical signal detector apparatus 112 includes only the epi-detector unit 196 and the resonant amplifier assembly 116 includes only the epi-resonant amplifier unit 204. Accordingly, this embodiment of the apparatus 100 forms an image of the sample 104 using only back-scattered photons from the sample 104. Similarly, in yet another embodiment of the optical imaging apparatus 100, the optical signal detector apparatus 112 includes only the forward detector unit 192 and the resonant amplifier assembly 116 includes only the forward resonant amplifier unit 200. Accordingly, this embodiment of the apparatus 100 forms an image of the sample 104 using only the forward-scattered photons from the sample 104.

The optical imaging apparatus 100 has been described above as a Stimulated Raman Loss (SRL) microscope. In another embodiment, however, the optical image apparatus implements an optical imaging technique based on transient absorption and/or photothermal effect. Both transient absorption and photothermal effect also require the extraction of a small AC signal at the sub-microvolt level from a noise environment making the resonant amplifier assembly 116 a useful and cost-effective alternative to the lock-in amplifier. Furthermore, the optical signal detector apparatus 112 has been described as including a forward detector unit 192 and an epi-detector unit 196, which are both heterodyne detector units. In another embodiment, the optical signal detector apparatus 112 includes other types of detector units, as desired by those of ordinary skill in the art.

In another embodiment of the resonant amplifier assembly 116, the bandpass filter 224, 296 is positioned between the preamplifier 216, 288 and the main amplifier 220, 292. Accordingly, the electrical output of the preamplifier 216, 288 is connected to the bandpass filter 224, 296, and the electrical output of the bandpass filter is connected to the main amplifier 220, 292. Positioning the bandpass filter 224, 296 between the preamplifier 216, 288 and the main amplifier 220, 292 enables the bandpass filter to filter out-of-band signals from the electrical signal, thereby preventing the out-of-band signals from saturating the main amplifier.

As described above, the optical imaging device 100 includes an acousto-optic modulator configured to control the intensity of the Stokes beam 152. In another embodiment, the optical imaging device 100 includes an electro-optic modulator or any other modulating device, as desired by those of ordinary skill in the art, that is capable of high frequency modulation in the MHz range of frequencies.

What is claimed is:
1. An optical imaging apparatus comprising:
an optical signal source configured (i) to generate an optical signal including a carrier signal and an imaging signal, and (ii) to guide said optical signal to a sample;
an optical signal detector apparatus configured (i) to detect a modified optical signal from said sample, and (ii) to generate an electrical image signal based on said modified optical signal, said electrical image signal including a background component and a modulated image signal corresponding to an image of said sample; and
a resonant amplifier assembly electrically coupled to said optical signal detector apparatus and configured (i) to isolate said modulated image signal from said background component, (ii) to amplify said modulated image signal, and (iii) to rectify said modulated image signal.

2. The optical imaging apparatus of claim 1, wherein:
said imaging signal is a Stokes beam having a first angular frequency,
said carrier signal is a pump beam having a second angular frequency, and
said first angular frequency is different than said second angular frequency.

3. The optical imaging apparatus of claim 2, wherein said optical signal source includes (i) a laser source configured to generate said pump beam and said Stokes beam, and (ii) an optical signal combiner optically coupled to said laser source and configured to optically combine said pump beam and said Stokes beam into a combined optical signal.

4. The optical imaging apparatus of claim 3, wherein said optical signal source further includes an acousto-optic modulator optically coupled to said laser source and said optical signal combiner and configured to modulate an intensity of said Stokes beam before said Stokes beam is combined with said pump beam by said optical signal combiner.

5. The optical imaging apparatus of claim 4, wherein said optical signal source further includes:
a laser scanning unit optically coupled to said optical signal combiner and configured to receive said combined optical signal, and
a polarization beam splitter optically coupled to said laser scanning unit and configured to receive said combined optical signal from said laser scanning unit.

6. The optical imaging apparatus of claim 5, wherein said optical signal detector apparatus includes at least one of:
a forward detector unit positioned to receive a forward-scattered component of said modified optical signal, and
an epi-detector unit optically positioned to receive a back-scattered component of said modified optical signal from said polarization beam splitter.

7. The optical imaging apparatus of claim 4, wherein:
said resonant amplifier assembly includes (i) a resonant tank circuit, and (ii) an amplifier electrically coupled to said resonant tank circuit,
said acousto-optic modulator is configured to modulate said Stokes beam at an optical modulation frequency, and
said resonant tank circuit is tuned to said optical modulation frequency.

8. The optical imaging apparatus of claim 7, wherein:
said resonant amplifier assembly further includes a bandpass filter electrically coupled to said amplifier, and
said bandpass filter has a center frequency that is approximately equal to said optical modulation frequency.

9. The optical imaging apparatus of claim 8, wherein said resonant amplifier assembly further includes a rectifier assembly electrically coupled to said bandpass filter.

10. The optical imaging apparatus of claim 9, wherein said amplifier of said resonant amplifier assembly includes:
a preamplifier electrically coupled to said resonant tank circuit, and
a main amplifier electrically coupled to said preamplifier and said bandpass filter.

11. A method of imaging a sample with an optical imaging apparatus comprising:
generating an optical signal including a carrier signal and an imaging signal with an optical signal source;
guiding said optical signal to the sample with said optical signal source;
detecting a modified optical signal from the sample with an optical signal detector apparatus;
generating an electrical image signal based on said modified optical signal with said optical signal detector apparatus, said electrical image signal including a background component and a modulated image signal corresponding to an image of the sample;
isolating said modulated image signal from said background component with a resonant amplifier assembly;
amplifying said modulated image signal with said resonant amplifier assembly; and
rectifying said modulated image signal with said resonant amplifier assembly.

12. The method of imaging a sample with an optical imaging apparatus of claim 11 further comprising:
modulating an intensity of said imaging signal with an acousto-optic modulator of said optical signal source to generate a modulated imaging signal; and
combining said modulated imaging signal with said carrier signal with an optical signal combiner of said optical signal source,
wherein said imaging signal is a Stokes beam generated by a laser source of said optical signal source, and
wherein said carrier signal is a pump beam generated by said laser source.

13. The method of imaging a sample with an optical imaging apparatus of claim 12, wherein:
said acousto-optic modulator is configured to modulate said Stokes beam at an optical modulation frequency,
said resonant amplifier assembly includes a resonant tank circuit, and
isolating said modulated image signal with a resonant amplifier assembly includes tuning said resonant tank circuit to said to said optical modulation frequency.

14. The method of imaging a sample with an optical imaging apparatus of claim 13, wherein:
amplifying said modulated image signal with said resonant amplifier assembly includes (i) amplifying said modulated image signal with a preamplifier of said resonant amplifier assembly, and (ii) amplifying said modulated image signal with a main amplifier of said resonant amplifier assembly,
said preamplifier is electrically coupled to said resonant tank circuit, and
said main amplifier is electrically coupled to said preamplifier.

15. The method of imaging a sample with an optical imaging apparatus of claim 14, wherein:
isolating said modulated image signal with a resonant amplifier assembly includes filtering said modulated image signal with a bandpass filter of said resonant amplifier assembly, and
said bandpass filter is electrically coupled to said preamplifier and said main amplifier.

16. The method of imaging a sample with an optical imaging apparatus of claim 11, wherein said rectifier assembly is electrically coupled to said bandpass filter.

17. The method of imaging a sample with an optical imaging apparatus of claim 11, wherein detecting said modified optical signal from the sample with said optical signal detector apparatus includes detecting at least one of (i) a forward-scattered component of said modified optical signal with a forward detector unit of said optical signal detector, and (ii) a back-scattered component of said modified optical signal with an epi-detector unit of said optical signal detector.

* * * * *